United States Patent [19]

Fujita et al.

[11] Patent Number: 4,873,351

[45] Date of Patent: Oct. 10, 1989

[54] METHOD FOR PREPARATION OF ANTIMONY MERCAPTIDES

[75] Inventors: Kohtaroh Fujita, Sakai; Toshio Wachi, Nara; Yoshiaki Ikeda, Sakai, all of Japan

[73] Assignee: Sakai Chemical Industry Co., Ltd., Osaka, Japan

[21] Appl. No.: 280,851

[22] Filed: Dec. 7, 1988

[51] Int. Cl.$^4$ .............................. C07F 9/90; C07F 9/92
[52] U.S. Cl. ..................................... 556/76; 556/77; 549/206; 549/210; 549/211
[58] Field of Search ................ 556/76, 77; 549/206, 549/210, 211

[56] References Cited

U.S. PATENT DOCUMENTS 4,279,806  7/1981  Murdrow .......................... 556/77 X
4,287,118  9/1981  Murdrow .......................... 556/77 X
4,303,578  12/1981  Michaelis ......................... 556/76 X

*Primary Examiner*—Paul F. Shaver
*Attorney, Agent, or Firm*—Wegner & Bretschneider

[57] ABSTRACT

Antimony trioxide is reached with an organic mercaptan $R^1$—SH or $R^2$—OCO—$(CH_2)_n$—SH (where $R^1$ is an alkyl, alkenyl, aryl, aralkyl, cycloalkyl or heterocyclic group having from 1 to 18 carbon atoms, which optionally has sulfide bond or ether bond or a hydroxyl or carboxyl group as a substituent, $R^2$ is a hydrogen atom or an alkyl, alkenyl, aryol, aralkyl, cycloalkyl or heterochclic group having from 1 to 18 carbon atoms, which optionally has sulfide bond or ether bond or a hydroxyl or carboxyl group as a substituent, and n is 1 to 3) in the presence of a lower aliphatic carboxylic acid to give an antimony mercaptide $Sb(-SR^1)_3$ or $Sb(-S-(CH_2)_n-COOR^2)_3$ of high purity with high yield. The products are excellent in the time-dependent stability and the effect as a passivator for catalysts for catalytic cracking of hydrocarbons.

4 Claims, No Drawings

METHOD FOR PREPARATION OF ANTIMONY MERCAPTIDES

FIELD OF THE INVENTION

The present invention relates to improved methods for preparation of antimony mercaptides and, in particular, to those for preparation of antimony mercaptides which are, for example, advantageously used in catalytic cracking of hydrocarbons as a passivator for passivating metals of certain kinds which are contained in the starting hydrocarbons and would have any harmful influence on the catalytic cracking catalyst used.

BACKGROUND OF THE INVENTION

In catalytic cracking of hydrocarbons, it is known that deposition of metals, such as nickel, vanadium, iron and the like, as contained in the starting hydrocarbons on the cracking catalyst used would lower the catalytic activity of the catalyst and additionally increase the amounts of hydrogen and coke formed to thereby decrease the yield of the desired useful components such as gasoline and so on. Accordingly, it has heretofore been known to use a so-called passivator of a compound of antimony, indium, bismuth or the like in catalytic cracking of hydrocarbons so as to passivate the aforesaid metals or to inactivate the same to thereby remove or reduce any harmful influence on the catalyst used, by various methods, for example, as described in U.S. Pat. Nos. 4,111,845, 4,153,536 and 4,257,919 and JP-A-104588 and 57-34188. (The term "JP-A" as used herein means an "unexamined published Japanese patent application".) In particular, it is known that various kinds of antimony compounds are excellent as the passivator for the purpose.

In addition to antimony trioxide and antimony pentoxide, such passivators include organic antimony compounds such as antimony tridecanoate, antimony tris(dithioacetate), antimony tris(p-toluenesulfonate), antimony tris(diphenylphosphite), antimony tris(o,o-dipropyldithiophosphate) and so on, which are described, for example, in JP-A-53-l04588. These passivators are used by dipping catalytic cracking catalysts in a solution containing the same or by adding the same to starting hydrocarbons.

Most of the organic antimony compounds are prepared by reaction of antimony trioxide in water or in an organic solvent. However, in accordance with the method of using such solvents, the reactor yield and, in its turn, the production yield are low. In particular, when water is used as a solvent, it is not easy to remove the water used from the reaction product formed, and the yield of the reaction product is also low. On the other hand, in order to obtain organic antimony compounds with high yield, for example, Czechoslovakian Pat. No. 221,707 illustrates a method of reacting antimony trioxide and a mercaptane in the presence of citric acid or salicylic acid. According to the said method, however, separation of such organic acid from the reaction product is not easy and the organic acid used would remain in the reaction product formed, so that it is difficult to obtain organic antimony compounds of high purity.

SUMMARY OF THE INVENTION

Accordingly, the subject matter of the present invention is to overcome the above-mentioned problems in the prior arts of preparing organic antimony compounds.

Specifically, the first object of the present invention is to provide a method of preparing antimony mercaptides of high purity with high yield by short time reaction at a relatively low temperature without using any solvent.

The second object of the present invention is to provide a method of preparing antimony mercaptides which are excellent in the oil-solubility and the time-dependent stability and which can advantageously be used as a passivator in catalytic cracking of hydrocarbons for effectively passivating any harmful metals, such as nickel, vanadium, iron and the like, which would be deposited on the catalytic cracking catalyst and would have any harmful influence on the said catalyst, to thereby maintain the high catalytic activity of the catalyst used so as to give the desired fractions with high yield in the catalytic cracking.

In accordance with the invention, there is first provided a method for preparation of antimony mercaptides of a general formula:

$$Sb(-SR^1)_3$$

where $R^1$ represents an alkyl, alkenyl, aryl, aralkyl cycloalkyl or heterocyclic group having from 1 to 18 carbon atoms, or an alkyl, alkenyl, aryl, aralkyl, cycloalkyl or heterocyclic group having from 1 to 18 carbon atoms and having sulfide bond or ether bond in the group or having a hydroxyl group or a carboxyl group as a substituent, which comprises reacting antimony trioxide and an organic mercaptan of a general formula:

$$R^1-SH$$

where $R^1$ has the same meaning as above, in the presence of a lower aliphatic carboxylic acid.

In accordance with the invention, there is secondarily provided a method for preparation of antimony mercaptides of a general formula:

$$Sb(-S-(CH_2)_n-COOR^2)_3$$

where $R^2$ represents a hydrogen atom, or an alkyl, alkenyl, aryl, aralkyl, cycloalkyl or heterocyclic group having from 1 to 18 carbon atoms, or an alkyl, alkenyl, aryl, aralkyl, cycloalkyl or heterocyclic group having from 1 to 18 carbon atoms and having sulfide bond or ether bond in the group or having a hydroxy group or a carboxyl group as a substituent, and n represents an integer of from 1 to 3, which comprises reacting antimony trioxide and an organic mercaptan of a general formula:

$$R^2-OCO-(CH_2)_n-SH$$

where $R^2$ and n have the same meaning as above, in the presence of a lower aliphatic carboxylic acid.

DETAILED DESCRIPTION OF THE INVENTION

The first method of the present invention of preparing antimony mercaptides is represented by the following reaction formula (1):

$$Sb_2O_3 + 6 R^1-SH \rightarrow 2 Sb(-SR^1)_3 + 3 H_2O \qquad (1)$$

The second method of the present invention of preparing antimony mercaptides is represented by the following reaction formula (2):

$$Sb_2O_3 + 6\ R^2-OCO-(CH_2)_n-SH \rightarrow 2\ Sb(-S-(CH_2)_n-COOR^2)_3 + 3\ H_2O \quad (2)$$

In accordance with the present invention, antimony trioxide is reacted with an organic mercaptan in the presence of a lower aliphatic carboxylic acid, as mentioned above. As the lower aliphatic carboxylic acid to be used in the said reactions, formic acid, acetic acid or propionic acid is preferred. The acid is generally used, in accordance with the present invention, in an amount falling within the scope of from 0.1 to 5 mols, preferably from 0.1 to 2 mols, per mol of antimony trioxide.

The said organic mercaptan is required to be reacted with antimony trioxide in a stoichiometrical amount or more per mol of antimony trioxide an,, preferably, in an amount falling within the scope of from 6.45 to 8 mols per mol of antimony trioxide.

The reaction temperature is generally 50° to 150° C., preferably 50° to 100° C. The reaction is completed generally in 1 to 3 hours. After the reaction, water formed and the aforesaid aliphatic carboxylic acid are removed by distillation and then the non-reacted antimony trioxide which will remain in a small amount is removed, whereby the desired antimony mercaptide having a high purity may be obtained with a high yield.

Now the methods of the present invention will be explained in detail hereunder, in accordance with the types of the organic mercaptan compounds used.

First, in accordance with the present invention, an organic mercaptan compound of a general formula (I):

$$HS-R^1 \quad (I)$$

where $R^1$ represents an alkyl, alkenyl, aryl, arylalkyl, cycloalkyl or heterocyclic group having from 1 to 18 carbon atoms, and the group may optionally have sulfide bond or ether bond therein or may optionally have a hydroxyl group or a carboxyl group as a substituent, is used to give an antimony mercaptide of a general formula (II):

$$Sb(-S-R^1) \quad (II)$$

where $R^1$ has the same meaning as above.

The above-mentioned organic mercaptan includes, for example, ethanethiol, n-propanethiol, isobutane-t-pentanethiol, hexanethiol, octanethiol, t-nonanethiol, t-dodecanethiol, t-tetradecanethiol, t-hexadecanethiol, oleylthiol, cyclohexanethiol, thiophenol, benzylthiol, etc.

Accordingly, antimony mercaptides (II) obtainable from the said organic mercaptan compounds include, when $R_1$ is an alkyl or alkenyl group, for example, antimony tris(mercaptoethyl), antimony tris(mercapto-n-propyl), antimony tris(mercaptoisobutyl), antimony tris(mercapto-n-amyl), antimony tris(mercaptohexyl), antimony tris(mercaptooctyl), antimony tris(mercaptononyl), antimony tris(mercaptododecyl), antimony tris(mercaptotetradecyl), antimony tris(mercaptohexadecyl), antimony tris(mercaptooleyl), etc.

When $R^1$ is an aryl group, for example, a phenyl group, antimony tris(mercaptophenyl) is mentioned; when $R^1$ is an arylakyl group, for example, a benzyl group, antimony tris(mercaptobenzyl) is mentioned; and when $R^1$ is a cycloalkyl group such as a cyclohexyl group, antimony tris(mercaptocyclohexyl) is mentioned.

In the said formula (I), $R^1$ may have sulfide bond or ether bond in the group. Accordingly, using organic mercaptan compounds of such type, the following antimony mercaptides (II) can be obtained. That is, when $R^1$ is an alkylthioalkyl group, there are obtained, for example, antimony tris(2-mercaptoethylethylsulfide), antimony tris(2-mercaptoethylbutylsulfide), antimony tris(2-mercaptoethyloctylsulfide), antimony tris(2-mercaptoethyldodecylsulfide), antimony tris(2-mercaptoethylstearylsulfide), etc.

Using organic mercaptan compounds where $R^1$ is an alkyloxyalkyl group, there are obtained, for example, antimony tris(2-mercaptoethylmethylether), antimony tris(2-mercaptoethylethylether), antimony tris(2-mercaptoethyl-n-butylether), antimony tris(2-mercaptoethylisobutylether), antimony tris(2-mercaptoethyl-2-ethylhexylether), etc.

Further, in the said formula (I), $R^1$ may have a hydroxyl group or a carboxyl group therein as a substituent. Accordingly, using organic mercaptan compounds of such type, there are obtained antimony mercaptides (II) which include, for example, antimony tris(2-mercaptoethanol), antimony tris(3-mercapto-1,2-propanediol), etc.

When an organic mercaptan compound where $R^1$ is a heterocyclic group, for example, 2-furfurylmercaptan is used, antimony tris(2-furfurylmercaptan) is obtained.

In accordance with another embodiment of the present invention, an organic mercaptan compound of a general formula (III):

$$R^2-OCO-(CH_2)_n-SH \quad (III)$$

where $R^2$ represents a hydrogen atom, or an alkyl, alkenyl, aryl, aralkyl, cycloalkyl or heterocyclic group having from 1 to 18 carbon atoms, or an alkyl, alkenyl, aryl, aralkyl, cycloalkyl or heterocyclic group having from 1 to 18 carbon atoms and having sulfide bond or ether bond in the group or having a hydroxyl group or a carboxyl group as a substituent, and n represents an integer of from 1 to 3, is used to give an antimony mercaptide of a general formula (IV):

$$Sb(-S-(CH_2)_n-COOR^2)_3 \quad (IV)$$

where $R^2$ and n have the same meanings as above.

Organic mercaptan compounds represented by the said formula (III) include, for example, 3-mercaptopropionic acid, thioglycolic acid, methyl 3-mercaptopropionate, butyl 3-mercaptopropionate, hexyl 3-mercaptopropionate, 2-ethylhexyl 3-mercaptopropionate, dodecyl 3-mercaptopropionate, oleyl 3-mercaptopropionate, butoxyethyl 3-mercaptopropionate, ethylthioethyl 3-mercaptopropionate, buthylthioethyl 3-mercaptopropionate, phenyl 3-mercaptopropionate, oleyl thioglycolate, etc.

Accordingly, antimony mercaptides of the said formula (IV) obtainable from the said organic mercaptan compounds of the formula (III) include, for example, antimony tris(3-mercaptopropionic acid), antimony tris(thioglycolic acid), antimony tris(methyl 3-mercaptopropionate), antimony tris(butyl 3-mercaptopropionate), antimony tris(hexyl 3-mercaptopropionate), antimony tris(2-ethylhexyl 3-mercaptopropionate), antimony tris(dodecyl 3-mercaptopropionate), antimony tris(stearyl 3-mercaptopropionate), antimony tris(oleyl 3-mercaptopropionate), antimony tris(allyl 3-mercaptopropionate), antimony tris(benzyl 3-mercaptopropionate), antimony tris(phenyl 3-mercaptopropionate), antimony tris(ethoxyethyl 3-mercaptopropionate), antimony tris(butoxyethyl 3-mercaptopropionate), antimony tris(methoxybutyl 3-mercaptopropionate, antimony tris(ethoxybutyl 3-mercaptopropionate), antimony tris(benzyl 3-mercaptopropionate, antimony tris(phenyl 3-mercaptopropionate), antimony tris(ethylthioethyl 3-mercaptopropionate), antimony tris(butylthioethyl 3-mercaptopropionate), antimony tris(methyl thioglycolate), antimony tris(oleyl thioglycolate), antimony tris(2-ethylhexyl thiglycolate), etc.

The antimony mercaptides obtainable by the methods of the present invention as mentioned above are advantageously used as a passivator in catalytic cracking of hydrocarbons. In particular, the antimony mercaptides obtainable by the methods of the present invention are excellent in the time-dependent stability and, even when containing excess mercaptans and other impurities, can effectively passivate the aforesaid harmful metals, so that the catalytic activity of the catalyst used in the said catalytic cracking may be kept high for a long period of time.

When the antimony mercaptides obtained by the present invention are used as a passivating agent, hydrocarbon-cracking catalysts may be dipped in a liquid containing the said antimony mercaptides singly or in the form of a mixture of two or more of them, or the said antimony mercaptides may be added to starting materials of hydrocarbons to be cracked, also singly or in the form of a mixture of two or more of them.

In general, catalytic cracking of hydrocarbons is effected generally at a temperature of from 500° to 600° C., while, on the other hand, all the antimony mercaptides obtainable by the present invention are decomposed under such temperature condition. Accordingly, although the mechanism of passivation of harmful metals on a catalyst by the said antimony mercaptides is not always clarified, it is believed that the antimony mercaptide is pyrolyzed and then the resulting antimony which would remain on the catalyst would passivate the harmful metals thereon.

In general, the amount of the passivator to be used in catalytic cracking of hydrocarbons further depends upon the amounts of metals, such as the aforesaid nickel, vanadium, iron and the like, as contained in the starting material hydrocarbons to be cracked as well as upon the catalytic cracking condition, etc. Although not specifically limited, the amount of the antimony mercaptide which is applied to a cracking catalyst is generally from about 0.1 to about 2 % by weight, as antimony, to the weight of the catalyst; and when the antimony mercaptide is added to the starting hydrocarbon, the amount thereof is generally from about 1 to about 10,000 ppm, especially from about 10 to 1,000 ppm, to the weight of the starting hydrocarbon.

The antimony mercaptides obtained by the methods of the present invention can be used in catalytic cracking of any conventional hydrocarbons. Catalytic cracking of hydrocarbons includes, for example, a process of heating petroleum hydrocarbons, such as light oil as a starting material, to a temperature of from about 500° to about 600° C. or so in the presence of a catalyst for catalytic cracking to give gasoline, liquefied petroleum gas, alkylated raw materials, intermediate fractions and so on, as well as fluid catalytic cracking of heavy petroleums containing bottom residues, the importance of the latter being increasing in these ways. The bottom residue-containing heavy petroleums as referred to herein mean those containing bottom residues such as asphalthene and so on, and these include normal pressure distillation bottom oil or reduced pressure distillation bottom oil of crude oil, crude oil and desulfurized crude oil. Especially, such heavy petroleums contain a large amount of the aforesaid metals and therefore the antimony mercaptides obtainable by the methods of the present invention are advantageously used as a passivator in catalytic cracking thereof. For catalytic cracking of such hydrocarbons are generally preferably used zeolite-modified silica-alumina catalysts, which, however, are not limitative.

As explained above, in accordance with the methods of the present invention, antimony mercaptides are prepared by reaction of antimony trioxide and an organic mercaptan compound in the presence of a lower aliphatic carboxylic acid. Accordingly, antimony mercaptides of high purity can be obtained without use of any solvent at a relatively low reaction temperature for a short reaction time with high yield. Since no solvent is used in the reaction, as mentioned above, the reactor yield and, in its turn, the production yield are high. In addition, the amount of the non-reacted antimony trioxide which would remain after reaction is only slight, so that the reaction product may easily be separated by filtration.

The antimony mercaptides thus obtained by the methods of the present invention can advantageously be used in catalytic cracking of hydrocarbons a passivator for the catalyst used, with no further purification treatment thereof. This is because, the antimony mercaptides obtained by the methods of the present invention can effectively passivate the aforesaid harmful metals, even though they contain any excess mercaptans or other impurities, so that the catalytic activity of the catalyst used in catalytic cracking of hydrocarbons can be maintained high for a long period of time.

In particular, antimony mercaptides of the aforesaid formulae (II) and (IV) where $R^1$ and $R^2$ are groups each having 4 or more carbon atoms are excellent in the oil-solubility and the time-dependent stability and therefore these are most preferably used as a passivator in catalytic cracking of hydrocarbons, whereupon these may effectively passivate the harmful metals as deposited on the catalyst used thereby to prevent formation of hydrogen or coke so that the desired useful fractions may be obtained with high yield.

Now the present invention will be explained in detail by reference to the following examples and referential examples, which, however, are not intended to restrict the scope of the present invention. The following referential examples show embodiments of use of antimony mercaptides obtained by the methods of the present invention as a passivator.

EXAMPLE 1

Preparation of antimony tris(2-ethylhexyl thioglycolate) in the presence of acetic acid 43.7 g (0.15 mol) of antimony trioxide, 197.7 g (0.97 mol) of 2-ethylhexyl thioglycolate and 5.46 g (0.09 mol) of acetic acid were fed in a four-neck flask and reacted at a temperature of 70° C. for 2 hours.

After the reaction, water formed and acetic acid were removed by distillation at 70° C. under reduced pressure of 25 mmHg, and then a slight amount of the remaining non-reacted antimony trioxide was filtered off with No. 5C filter paper. Thus an yellow transparent liquid of antimony tris(2-ethylhexyl thioglycolate) was obtained. The yield was 232.0 g, the antimony content was 15.5 %, and the refractive index $n_D^{25}$ was 1.5232. The amount of acetic acid in the product antimony mercaptide was 0.03 %.

The acetic acid as recovered by the said reduced pressure distillation was 98.0 % of the amount as initially fed, the water formed was 98.7 % of the theoretical amount, and the non-reacted antimony trioxide was 0.1 g.

EXAMPLE 2

Preparation of antimony tris(2-ethylhexyl 3-mercaptopropionate) in the presence of acetic acid 43.7 g (0.15 mol) of antimony trioxide, 254.9 g (1.17 mols) of 2-ethylhexyl 3-mercaptopropionate and 10.9 g (0.18 mol) of acetic acid were fed into a four-neck flask and reacted at a temperature of 80° C. for 2 hour.

After the reaction, water formed and acetic acid were removed by distillation at 80° C. under reduced pressure of 25 mmHg, and then a slight amount of the remaining non-reacted antimony trioxide was filtered off with No. 5C filter paper. Thus an yellow transparent liquid of antimony tris(2-ethylhexyl 3-mercaptopropionate) was obtained. The yield was 288.2 g, the antimony content was 14.0 %, and the refractive index $n_D^{25}$ was 1.5114. The amount of acetic acid in the product antimony mercaptide was 0.03 %.

The acetic acid recovered by the said reduced pressure distillation was 99.2 % of the amount as initially fed, the water formed was 99.3 % of the theoretical value, and the non-reacted antimony trioxide was 0.1 g.

EXAMPLE 3

Preparation of antimony tris(t-decylmercaptan) in the presence of acetic acid 43.7 g (0.15 mol) of antimony trioxide, 187.9 g (0.93 mol) of t-dodecylmercaptan and 0.90 g (0.015 mol) of acetic acid were fed in a four-neck flask and reacted at a temperature of 70° C. for 2 hours.

After the reaction, water formed and acetic acid were removed by distillation at 70° C. under reduced pressure of 25 mmHg, and then a slight amount of the remaining non-reacted antimony trioxide was filtered off with No. 5C filter paper. Thus an yellow transparent liquid of antimony tris(t-dodecylmercaptan) was obtained. The yield was 222.4 g, the antimony content was 14.1 %, and the refractive index $n_D^{25}$ was 1.5304. The amount of acetic acid in the product antimony mercaptide was 0.02 %.

The acetic acid recovered by the said reduced pressure distillation was 98.0 % of the amount as initially fed, the water formed was 99.0 % of the theoretical value, and the non-reacted antimony trioxide was 0.2 g.

EXAMPLE 4

Preparation of antimony tris(2-ethylhexyl thioglycolate) in the presence of formic acid 43.7 g (0.15 mol) of antimony trioxide, 197.7 g (0.97 mol) of 2-ethylhexyl thioglycolate and 4.14 g (0.09 mol) of formic acid were fed in a four-neck flask and reacted at a temperature of 75° C. for 2 hours Subsequently, the same procedure as in Example 1 was repeated to obtain 231.0 g of antimony tris(2-ethylhexyl thioglycolate). The amount of formic acid in the antimony mercaptide was 0.01 %.

The amount of the formic acid recovered was 98.0 % of the amount as initially fed, the water formed was 99.0 % of the theoretical value, and the non-reacted antimony trioxide was 0.1 g.

EXAMPLE 5

Preparation of antimony tris(2-ethylhexyl thioglycolate) in the presence of formic acid 43.7 g (0.15 mol) of antimony trioxide, 197.7 g (0.97 mol) of 2-ethylhexyl thioglycolate and 10.3 g (0.22 mol) of formic acid were fed in a four-neck flask and reacted at a temperature of 72° C. for 2 hours.

Subsequently, the same procedure as in Example 1 was repeated to obtain 231.5 g of antimony tris(2-ethylhexyl thioglycolate). The amount of formic acid in the antimony mercaptide was 0.01 %.

The amount of the formic acid recovered was 99.0 % of the amount as initially fed, the water formed was 99.2 % of the theoretical value, and the non-reacted antimony trioxide was 0.1 g.

EXAMPLE 6

Preparation of antimony tris(2-ethylhexyl thioglycolate) in the presence of propionic acid 43.7 g (0.15 mol) of antimony trioxide, 197.7 g (0.97 mol) of 2-ethylhexyl thiolgycolate and 5.55 g (0.075 mol) of propionic acid were fed in a four-neck flask and reacted at a temperature of 80° C. for After the reaction, water formed and propionic acid were removed by distillation at a temperature of 80° C. under reduced pressure of 25 mmHg, and then the final temperature was further elevated up to 105° C. under the same pressure to completely remove the remaining propionic acid.

Subsequently, the same procedure as in Example 1 was repeated to obtain 231.2 g of antimony tris(2-ethylhexyl thioglycolate). The amount of propionic acid in the antimony mercaptide was 0.04 %.

The amount of the propionic acid recovered was 98.5 % of the amount as initially fed, the water formed was 99.4 % of the theoretical value, and the non-reacted antimony trioxide was 0.1 g.

EXAMPLE 7

Preparation of antimony tris(2-ethylhexyl thioglycolate in the presence of propionic acid 43.7 g (0.15 mol) of antimony trioxide, 197.7 g (0.97 mol) of 2-ethylhexyl thioglycolate and 22.2 g (0.30 mol) of propionic acid were fed in a four-neck flask and reacted at a temperature of 75° C. for 2 hours.

After the reaction, water formed and propionic acid were removed by distillation at a temperature of 80° C. under reduced pressure of 25 mmHg, and then the final temperature was further elevated up to 105° C. under the same pressure to completely remove the remaining propionic acid.

Subsequently, the same procedure as in Example 1 was repeated to obtain 230.9 g of antimony tris(2-ethylhexyl thioglycolate). The amount of propionic acid in the antimony mercaptide was 0.04 %.

The amount of the propionic acid recovered was 99.0 % of the amount as initially fed, the water formed was 99.3 % of the theoretical value, and the non-reacted antimony trioxide was 0.1 g.

COMPARATIVE EXAMPLE 1

Preparation of antimony tris(2-ethylhexyl thioglycolate) in the presence of no aliphatic carboxylic acid

43.7 g (0.15 mol) of antimony trioxide and 205.2 g (1.00 mol) of 2-ethylheyxl thioglycolate were fed in a four-neck flask and reacted at a temperature of 75° C. for 2 hours.

After the reaction, water formed was removed by distillation at 75° C. under reduced pressure of 25 mmHg, and then the non-reacted antimony trioxide was filtered off with No. 5C filter paper by the aid of KC Floc as a filtration aid. Thus an yellow transparent liquid of antimony tris(2-ethylhexyl thioglycolate) was obtained. When the said filtration aid was not used, the non-reacted antimony trioxide could not be filtered off through No. 5C filter paper.

The yield was 237 g, the antimony content was 11.9 %, and the refractive index $n_D^{25}$ was 1.5162. The water formed was 66.5 % of the theoretical value, and the non-reacted antimony trioxide was 5.2 g.

COMPARATIVE EXAMPLE 2

Preparation of antimony tris(2-ethylhexyl thioglycolate) in the presence of too small amount of acetic acid

43.7 g (0.15 mol) of antimony trioxide, 205.2 g (1.00 mol) of 2-ethylhexyl thioglycolate and 0.46 g (0.0077 mol) of acetic acid were fed in a four-neck flask and reacted at a temperature of 75° C. for 2 hours.

After the reaction, water formed and acetic acid were removed by distillation at 75° C. under reduced pressure of 25 mmHg, and then the non-reacted antimony trioxide was filtered off with No. 5C filter paper by the aid of KC Floc as a filtration aid. Thus an yellow transparent liquid of antimony tris(2-ethylhexyl thioglycolate) was obtained. When the said filtration aid was not used, the non-reacted antimony trioxide could not be filtered off through No. 5C filter paper.

The yield was 236.0 g, the antimony content was 11.9 %, and the refractive index $n_D^{25}$ was 1.5163. The water formed was 66.3 % of the theoretical value, and the non-reacted antimony trioxide was 5.0 g.

REFERENTIAL EXAMPLE 1

In a fluid catalytic cracking pilot apparatus using a silica-alumina fluid catalytic cracking catalyst containing about 5 % by weight of zeolite, normal pressure distillation bottom oil (from Middle East) containing 50 ppm of nickel, 200 ppm of vanadium and 10 % of residual carbon was catalytically cracked whereby nickel and vanadium were deposited on the catalyst. The catalyst was taken out from the apparatus and analyzed and, as a result, the catalyst was found to have 2300 ppm of nickel and 7000 ppm of vanadium.

Next, the catalyst was filled in a fixed-bed microreactor and the same normal pressure distillation bottom oil as above, to which the passivator of the present invention had been added in an amount of 100 ppm as antimony, was catalytically cracked therein, and the catalytic activity of the catalyst used was determined. For comparison, the normal pressure distillation bottom oil was catalytically cracked in the same manner without addition of the passivator, and the catalytic activity of the catalyst used was also determined. The results were shown in Table 1 below.

TABLE 1

| | Test No. | Passivator Structural Formula | Microreactor Test Result | | | |
|---|---|---|---|---|---|---|
| | | | Sb-content (wt. %) | Conversion (wt. %) | Formation of Carbon (C.P.F) | Amount of Hydrogen Generated ($H_2/CH_4$) |
| Referential Example 1 | 1 | $Sb(-S-C_8H_{17})_3$ | 19.5 | 62 | 2.0 | 0.8 |
| | 2 | $Sb(-S-t-C_{12}H_{25})_3$ | 14.1 | 56 | 2.5 | 1.1 |
| | 3 | $Sb(-S-C_2H_4-COOC_8H_{17})_3$ | 14.0 | 63 | 2.1 | 0.9 |
| | 4 | $Sb(-S-CH_2-COOC_8H_{17})_3$ | 15.5 | 63 | 1.9 | 0.9 |
| | 5 | $Sb(-S-CH_2-COOCH_3)_3$ | 25.0 | 61 | 2.3 | 1.0 |
| | 6 | $Sb(-S-C_2H_4-COOC_4H_9)_3$ | 18.5 | 66 | 2.1 | 1.1 |
| | 7 | $Sb(-S-CH_2-COOC_{18}H_{35})_3$ | 9.0 | 60 | 2.3 | 1.1 |
| | 8 | None | — | 50 | 3.0 | 1.5 |

Note: $C_8H_{17}$ group in the passivator was n-octyl group in the test No. 1 and 2-ethylhexyl group in the test Nos. 3 and 4.

REFERENTIAL EXAMPLE 2

The passivator shown in Table 2 below was applied to a silica-alumina fluid catalytic cracking catalyst containing about 5 % by weight of zeolite by spray-dry method. The amount of the passivator as applied to the catalyst was 0.8 % by weight of the catalyst, as antimony.

The thus passivator-applied catalyst was filled in a fixed-bed microreactor and the same normal pressure distillation bottom oil as that used in Referential Example 1 was catalytically cracked therein for 100 hours, whereupon the catalytic activity of the catalyst used was checked. For comparison, no passivator was applied to the catalyst, which was used in the same catalytic cracking, and the catalytic activity was also checked. The results were shown in Table 2.

TABLE 2

| | Test No. | Passivator Structural Formula |
|---|---|---|
| Referential Example 2 | 1 | $Sb(-S-t-C_{12}H_{25})_3$ |
| | 2 | $Sb(-S-C_2H_4-COOC_8H_{17})_3$ |
| | 3 | $Sb(-S-CH_2-COOC_8H_{17})_3$ |
| | 4 |  |
| | 5 | None |

Note: $C_8H_{17}$ group in the passivator was 2-ethylhexyl group.

REFERENTIAL EXAMPLE 3

In order to evaluate the solubility (in hydrocarbons) of the antimony tris(2-ethylhexyl thioglycolate) having antimony content of 15.5 %, the antimony tris(2-ethylhexyl 3-mercaptopropionate) having antimony content of 14.0 % and the antimony tris(t-dodecylmercaptan) having antimony content of 14.1 % obtained in Example 1, 2 and 3, respectively, 1 g of each of the said passivators was added to 100 g of A-heavy oil/light oil mixture (3/7, by volume) at room temperature and shaken, and then the solubility was observed with the eye. As a result, it was confirmed that all of the said passivators were dissolved in the said hydrocarbon.

For comparison, antimony tris(thioacetate) having antimony content of 35 % by weight was subjected to the same solubility test and, as a result, it was confirmed that this was not dissolved in the said hydrocarbon.

REFERENTIAL EXAMPLE 4

This is to clarify the matter as to whether the amount of the acetic acid and organic mercaptan per the amount of the antimony trioxide used in preparation of antimony mercaptides would have any influence on the time-dependent stability of the antimony mercaptide obtained and the effect thereof as a passivator.

The same procedure as the Example 1 was repeated except that the amount of the acetic acid and that of the 2-ethylhexyl 3-mercaptopropionate were varied as shown in Table 3, on the basis of the amount of the antimony trioxide, and a reaction product of an yellow transparent liquid containing the antimony mercaptide formed was obtained almost quantitatively.

Each of the thus prepared antimony mercaptide products was sealed and shielded from light at room temperature and left to stand as such. Formation of precipitates, if any, was observed at regular intervals, whereby the time-dependent stability of the products was evaluated. In addition, the effect of each product as a passivator was evaluated in the same manner as in Referential Example 1. The results were shown in Table 3.

products of the invention but this was poor in the time-dependent stability.

When 4 mols of acetic acid and 6.45 mols of the organic mercaptan were used per mol of antimony trioxide as in Test No. 3 in Table 3, the reaction product obtained was almost same as the reaction products obtained in Test Nos. 1 and 2, and the former had almost the same time-dependent stability and effect as a passivator as the latter.

What is claimed is:

1. A method for preparation of antimony mercaptides of a general formula:

$$Sb(-SR^1)_3$$

where $R^1$ represents an alkyl, alkenyl, aryl, aralkyl, cycloalkyl or heterocyclic group having from 1 to 18 carbon atoms, or an alkyl, alkenyl, aryl, aralkyl, cycloalkyl or heterocyclic group having from 1 to 18 carbon atoms and having sulfide bond or ether bond in the group or having a hydroxyl group or a carboxyl group as a substituent, which comprises reacting antimony trioxide and an organic mercaptan of a general formula:

$$R^1-SH$$

where $R^1$ has the same meaning as above, in the presence of a lower aliphatic carboxylic acid.

2. A method for preparation of antimony mercaptides as claimed in claim 1, in which the lower aliphatic carboxylic acid is formic acid, acetic acid or propionic acid.

3. A method for preparation of antimony mercaptides of a general formula:

$$Sb(-S-(CH_2)_n-COOR^2)_3$$

TABLE 3

| | Test No. | Molar Ratio of Reactants | | | Sb-Content (wt. %) | Time-dependent Stability(*) | Microreactor Test Result | | |
|---|---|---|---|---|---|---|---|---|---|
| | | Antimony Trioxide | Acetic Acid | Mercaptan | | | Conversion (wt. %) | Formation of Carbon (C.P.F.) | Amount of Hydrogen Generated ($H_2/CH_4$) |
| Referential | 1 | 1.00 | 0.60 | 6.45 | 15.5 | O | 61 | 2.0 | 0.9 |
| Example 4 | 2 | 1.00 | 1.21 | 7.80 | 14.0 | O | 60 | 2.1 | 1.0 |
| | 3 | 1.00 | 4.00 | 6.45 | 15.5 | O | 61 | 2.0 | 0.9 |
| | 4 | 1.00 | 0.00 | 6.45 | 11.9 | O | 57 | 2.5 | 1.3 |
| | 5 | 1.00 | 0.05 | 6.45 | 11.9 | O | 55 | 2.6 | 1.3 |
| | 6 | 1.00 | 0.60 | 6.00 | 15.8 | X | 60 | 2.0 | 0.9 |

Note (*): "O" indicates formation of no precipitate after 6 months; and "X" indicates formation of precipitates after 12 days.

As is obvious from the results shown in Table 3, all the antimony mercaptides of Test Nos. 1, 2 and 3, which were prepared in accordance with the method of the present invention, were excellent in the time-dependent stability and the effect as a passivator.

As opposed to this, in the case of Test Nos. 4 and 5 where acetic acid was used in a smaller amount than 0.1 mol per mol of antimony trioxide, the products were excellent in the time-dependent stability but these could not sufficiently prevent the lowering of the catalytic activity.

In this case, since a relatively large amount of a substance which might be considered to be the non-reacted antimony trioxide remained after the reaction, the time-dependent stability was determined on the liquid obtained by removing the non-reacted substance from the reaction product after the reaction.

On the other hand, when the organic mercaptan was used in an exactly stoichiometrical amount to the antimony trioxide as in Test No. 6, the effect of the product as a passivator had no great difference from that of the where $R^2$ represents a hydrogen atom, or an alkyl, alkenyl, aryl, aralkyl, cycloalkyl or heterocyclic group having from 1 to 18 carbon atoms, or an alkyl, alkenyl, aryl, aralkyl, cycloalkyl or heterocyclic group having from to 18 carbon atoms and having sulfide bond or ether bond in the group or having a hydroxyl group or a carboxyl group as a substituent, and n represents an integer of from 1 to 3, which comprises reacting antimony trioxide and an organic mercaptan of a general formula:

$$R^2-OCO-(CH_2)_n-SH$$

where $R^2$ and n have the same meanings as above, in the presence of a lower aliphatic carboxylic acid.

4. A method for preparation of antimony mercaptides as claimed in claim 3, in which the lower aliphatic carboxylic acid is formic acid, acetic acid or propionic acid.

* * * * *